(12) United States Patent
Hubble, III et al.

(10) Patent No.: US 7,259,853 B2
(45) Date of Patent: Aug. 21, 2007

(54) SYSTEMS AND METHODS FOR AUGMENTING SPECTRAL RANGE OF AN LED SPECTROPHOTOMETER

(75) Inventors: Fred F. Hubble, III, Friendswood, TX (US); Lalit K. Mestha, Fairport, NY (US); Daniel A. Robbins, Williamson, NY (US); Tonya L. Love, Rochester, NY (US)

(73) Assignee: Xerox Corporation, Stamford, CT (US)

( * ) Notice: Subject to any disclaimer, the term of this patent is extended or adjusted under 35 U.S.C. 154(b) by 300 days.

(21) Appl. No.: 11/017,652

(22) Filed: Dec. 22, 2004

(65) Prior Publication Data

US 2006/0132777 A1   Jun. 22, 2006

(51) Int. Cl.
*G01J 3/46* (2006.01)
(52) U.S. Cl. ..................................... 356/402; 356/319
(58) Field of Classification Search ................. 356/402, 356/420
See application file for complete search history.

(56) References Cited

U.S. PATENT DOCUMENTS

| | | | |
|---|---|---|---|
| 6,384,918 B1 | 5/2002 | Hubble, III et al. | |
| 6,449,045 B1 | 9/2002 | Mestha | |
| 6,584,435 B2 | 6/2003 | Mestha et al. | |
| 6,621,576 B2 | 9/2003 | Tandon et al. | |
| 6,633,382 B2 | 10/2003 | Hubble, III et al. | |
| 6,639,669 B2 | 10/2003 | Hubble, III et al. | |
| 6,721,629 B2 | 4/2004 | Wendling et al. | |
| 2002/0159066 A1* | 10/2002 | Berstis | 356/406 |
| 2003/0142314 A1 | 7/2003 | Hubble, III et al. | |
| 2003/0169421 A1* | 9/2003 | Ehbets | 356/328 |
| 2003/0227626 A1* | 12/2003 | Dobbs et al. | 356/407 |
| 2004/0247484 A1* | 12/2004 | Yerazunis | 422/82.05 |

OTHER PUBLICATIONS

U.S. Appl. No. 10/758,096, filed Jan. 16, 2004, Lalit K. Mestha et al.

* cited by examiner

*Primary Examiner*—Gregory J. Toatley, Jr.
*Assistant Examiner*—Kara Geisel
(74) *Attorney, Agent, or Firm*—Oliff & Berridge, PLC

(57) ABSTRACT

An LED spectrophtometer device for determining an aspect of the color of an object may include: a visible spectrophotometer comprising a plurality of light emitting diodes that emit light in the visible spectrum onto the object; at least one detector for detecting said light after being directed onto the object and for generating an output; and a UV light emitting diode assembly that emits light in the near ultraviolet spectrum and communicates with at least one detector for generating an output. The device may further include a processor that combines the outputs of the at least one detector of the visible spectrophotometer and the at least one detector in communication with the UV light emitting diode assembly.

18 Claims, 8 Drawing Sheets

SYSTEMS AND METHODS FOR AUGMENTING SPECTRAL RANGE OF AN LED SPECTROPHOTOMETER

RELATED APPLICATIONS

Cross-reference and incorporation by reference is made to the following copending and commonly assigned U.S. Patent Application Publication No. 2003/0055611 A1.

BACKGROUND

1. Field

This invention relates to the field of spectrophotometry.

2. Description of Related Art

Automatic stand-alone color calibration systems employ spectrophotometers mounted in the path of a moving substrate, such as, for example, paper, moving in a path in marking devices, preferably in the output path of the marking device. In electrophotographic marking devices, spectrophotometers may be located downstream of the fusing or drying components of the device, without having to otherwise modify the marking device, or interfere with or interrupt normal marking, or the movement of the marked sheets in the substrate path, and yet provide accurate color measurements of test color patches printed on the moving sheets as they pass the spectrophotometer. Automatic stand-alone color calibration systems enable a complete closed loop color control of a marking device.

Typically, spectrophotometers give color information in terms of measured reflectances or transmittances of light, at different wavelengths of light, from a test surface. A spectrophotometer desirably provides distinct electric signals corresponding to the different levels of reflected light received from the respective different illumination wavelength ranges or channels.

Known devices capable of providing distinct electric signals corresponding to the different levels of reflected light received from the respective different illumination wavelength ranges or channels include LED based sensors marketed by Color Savvy® or Accuracy Microsensor. LED spectrophotometers, such as those shown in Laser Focus World, June 2003, "Color Sensor Enables Closed Loop Control" by John Wallace and U.S. Pat. Nos. 6,384,918 and 6,633,382, each of which is incorporated herein by reference in its entirety, may be used for color measurement in embedded systems. However, these devices may provide inaccurate spectrophotometric measurements regarding substrates which contain fluorescent whitening agents (FWA).

During the papermaking process, a variety of cleaning and bleaching steps are performed by paper manufacturers on paper pulp in order to increase the whiteness of the paper. Despite cleaning and bleaching, all conventional papers exhibit slightly lower reflectance in the blue region of the spectrum, and, therefore appear to the human eye to be slightly yellow or tan in color. For this reason, most high quality papers intended to be used for color reprographics contain one or more additives generally referred to as fluorescent whitening agents (FWA) or, more generally, "whiteners". These additives, added early in the papermaking process, absorb light in the ultraviolet (UV) portion of the spectrum (including wavelengths of 330-390 nm) that is reemitted in the visible band, including the blue portion of the spectrum (e.g., at wavelengths of 400-500 nm). This makes the manufactured paper appear whiter, and color images printed thereon appear more saturated and therefore more colorful.

For example, high quality bond papers used in the reprographic industry fluoresce in the blue region when exposed to broadband illumination containing UV. Many conventional LED spectrophotometers contain no UV lamps, and, as a result, the appearance of the bond papers as measured by conventional LED spectrophotometers varies from the appearance of the same bond papers as measured by spectrophotometers with broadband light sources that include ultraviolet.

The Xerox® inline spectrophotometers use an array of 8 light emitting diodes (LEDs) to illuminate test targets printed on paper. LED spectrophotometers have a cost advantage over spectrophotometers using non-LED light sources such as, for example, incandescent lamps and xenon flash lamps, because LEDs are stable, small, low cost, and easily driven, as compared to incandescent lamps and xenon Flash lamps.

Ocean Optics™ provides LED light source spectrophotometers which use Ocean Optics LED light sources, including visible LEDs, or an ultraviolet LED which may be substituted for a visible wavelength LED, and which emits at 380 nanometers; however, Ocean Optics™ discloses using one LED light source in a spectrophotometer light source unit.

The following is an attempt to provide some simplified clarifications relating and distinguishing the respective terms "spectrophotometer," "colorimeter," and "densitometer," as they may be used in the specific context of specification examples of providing components for an on-line color printer color correction system, but not necessarily as claim limitations.

Typical prior spectrophotometers in this context use 16 or 32 channels measuring from approximately 400 nm to 700 nm, to cover the humanly visible color spectra or wavelength range. A typical spectrophotometer gives color information in terms of measured reflectances or transmittances of light, at the different wavelengths of light, from the test surface. The spectrophotometer desirably provides distinct electrical signals corresponding to the different levels of reflected light from the respective different illumination wavelength ranges or channels.

A "colorimeter" normally has three illumination channels, red, green and blue. That is, generally, a "colorimeter" provides its three (red, green and blue or "RGB") values as read by a light sensor or detector receiving reflected light from a color test surface sequentially illuminated with red, green and blue illuminators, such as three different color LEDs or one white light lamp with three different color filters. It may thus be considered different from, or a limited special case of, a "spectrophotometer," in that it provides output color information in the trichromatic quantity known as RGB.

Trichromatic quantities may be used for representing color in three coordinate space through some type of transformation. Other RGB conversions to "device independent color space" (i.e., RGB converted to conventional L*a*b*) typically use a color conversion transformation equation or a "lookup table" system in a known manner.

A "densitometer" typically has only a single channel, and simply measures the amplitude of light reflectivity from the test surface, such as a developed toner test patch on a photoreceptor, at a selected angle over a range of wavelengths, which may be wide or narrow. A single illumination source, such as an IR LED, a visible LED, or an incandescent lamp, may be used. The output of the densitometer detector is programmed to give the optical density of the sample. A densitometer of this type is basically "color blind." For example, a cyan test patch and magenta test patch could have the same optical densities as seen by the densitometer, but, of course, exhibit different colors.

Thus, a spectrophotometer differs from both a colorimeter and a densitometer.

SUMMARY

Exemplary systems and methods use an ultra-violet (UV) LED light source to measure the reflectance spectra in spectrophotometers and/or spectrophotometer attachments.

Various exemplary implementations may be considered to belong to a special class of spectrophotometers which illuminate their target with light in the range of approximately 300 to 700 nm, and are to be distinguished from spectrophotometers with wide-band illumination sources, such as, for example, flashed Xenon lamp spectrophotometers, or incandescent lamp spectrophotometers. LED spectrophotometers require a spectral reconstruction database. For example, see U.S. Pat. Nos. 6,584,435 and 6,449,045.

For a low cost implementation of a color sensor, a multiple illuminant device may be used as the illumination source, and may have, for example, 8, 10, 12 or 16 LEDs. Each LED may be selected to have a narrow band emission curve in spectral space. Therefore, for example, light from eight LEDs reflected by a substrate would correspond to eight separate spectral measurement points of a reflectance curve of that substrate. The LEDs, or other multiple illuminant based color sensor equivalent, such as lasers, may be switched on one at a time as, for example, measured media is passed through a transport of a printer. The reflected light may then be detected by one or more photodetectors and a corresponding voltage may be integrated and normalized, for example, with a priori measurements of a white tile.

UV LEDs may be advantageously utilized, for example, in a fluorescence illuminator and sensor that is used in conjunction with visible LED based colorimeters and/or spectrophotometers to sense the amount of fluorescence, for example, of reprographic papers, enabling corrections to be made to the measured color coordinates to account for the fluorescence under broadband illumination. The fluorescence illuminator and sensor may be provided as a physically separate attachment for a conventional LED visible spectrophotometer or may be integrated into the conventional LED visible spectrophotometer.

UV LEDs may be used to provide trigger information when used as fiduciary mark sensors. For example, such a use is described in U.S. Pat. No. 6,639,669 to Hubble III et al.

A low cost means of measuring the fluorescence of paper in a reprographic engine may be accomplished according to various implementations.

Improved accuracy of conventional LED spectrophotometers may be accomplished according to various implementations.

Low cost LED light sources may be used, for example, in colorimeters and/or spectrophotometers where increased accuracy and/or increased agreement with broadband based instruments is desired.

Improved accuracy in the measurement of fluorescence samples may be achieved according to various implementations, thereby reducing the number of databases personalized to a particular fluorescent level.

The existence of fluorescence, for example, in non-graphic arts applications such as paints, dyes, clothing, etc., may be accomplished according to various implementations.

One or more UV LEDs may be added to conventional non-UV capable spectrophotometers.

Spectrophotometric curves of substrates, such as, for example, papers, that contain fluorescent whitening agents, may be corrected.

These and other objects, advantages and salient features are described in or apparent from the following detailed description.

BRIEF DESCRIPTION OF THE DRAWINGS

Various details are described with reference to the drawings, wherein like numerals represent like parts, and wherein.

DETAILED DESCRIPTION OF EXEMPLARY EMBODIMENTS

Figure 1:
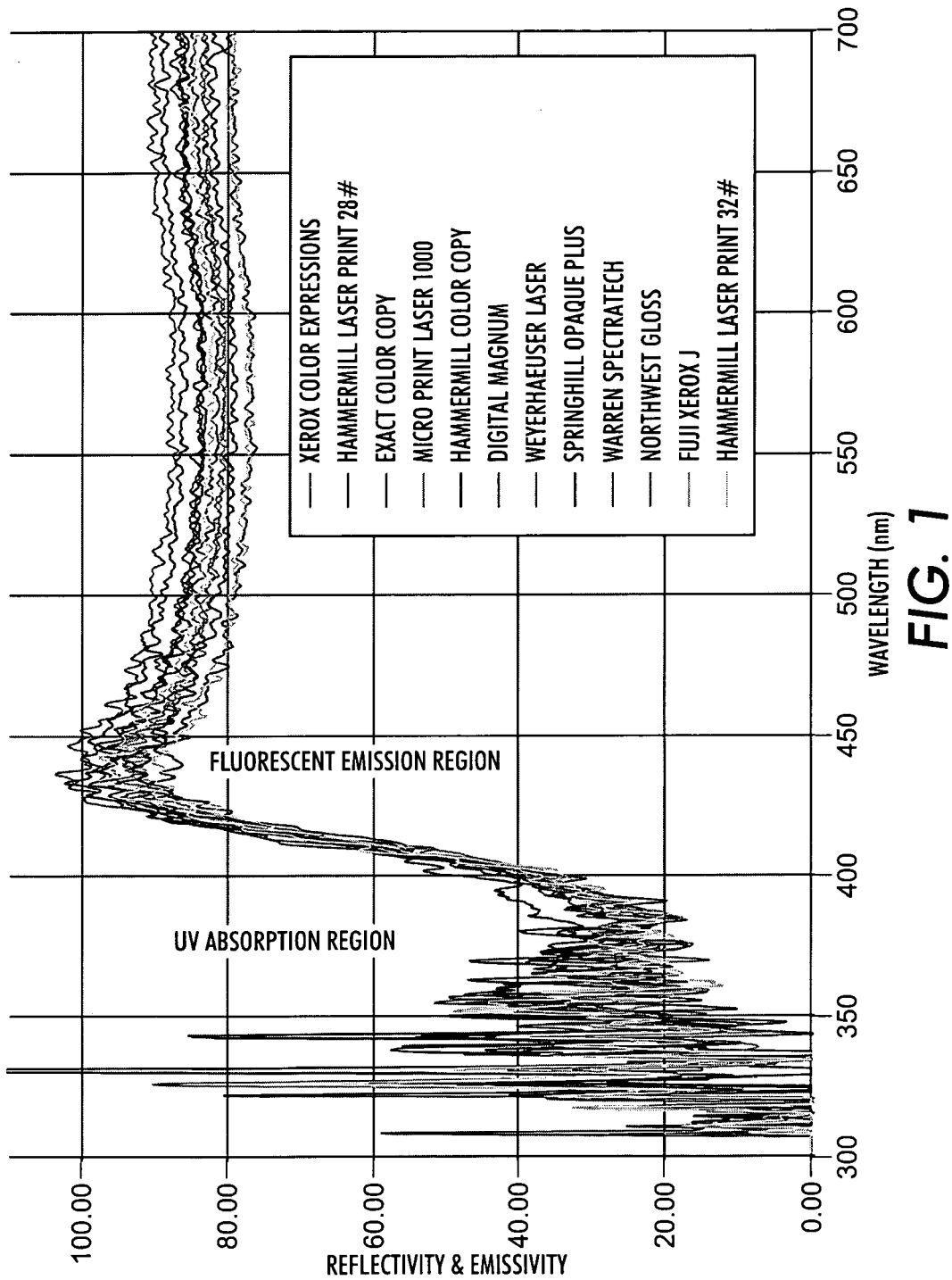
FIG. 1 shows the reflectance spectra of twelve types of bond color reprographic papers measured with a spectrophotometer equipped with a quartz halogen lamp at a light source at a color temperature of 3300° K.

A UV LED spectrophotometer may be especially suitable for being mounted at one side of the printed sheets output path of a color printer to optically evaluate color imprinted output sheets as they move past the spectrophotometer, variably spaced therefrom, without having to contact the sheets or interfere with the normal movement of the sheets. In particular, such a UV LED spectrophotometer may be used to measure a number of color test patch samples printed by the printer on actual printed sheet output of the printer during regular or selected printer operation intervals (between normal printing runs or print jobs). Such color test sheet printing intervals may be at regular timed intervals, and/or at each machine "cycle-up," or as otherwise directed, for example, by the system software. The spectrophotometer may be mounted at one side of the paper path of the machine, or, if it is desired to use duplex color test sheets, two spectrophotometers may be mounted on opposite sides of the paper path.

Relatively frequent color calibration of a color printer is highly desirable, since the colors actually printed on the output media (as compared to the colors intended to be printed) can significantly change, or drift out of calibration over time, for various known reasons. For example, changes in the selected or loaded print media, such as differences paper or plastic sheet types, materials, weights, calendaring, coating, humidity, etc., or changes in the printer's ambient conditions, changes in the image developer materials, aging or wear of printer components, varying interactions of different colors being printed, etc. Printing test color patches on test sheets of the same print media under the same printing conditions during the same relative time periods as the color print job being color-controlled is thus very desirable.

It is thus also advantageous to provide dual-mode color test sheets, in which multiple color patches of different colors are printed on otherwise blank areas of each, or selected, banner, cover, or other inter-document or print job separator sheets. Different sets of colors may be printed on different banner or other test sheets. This dual use of such sheets saves both print paper and printer utilization time, and also provides frequent color calibration opportunities where the printing system is one in which banner sheets are being printed at frequent intervals anyway.

The spectrophotometer may tailor or set the particular colors or combinations of the test patches on a particular banner or other test sheet to those colors which are about to be printed on the specific document for that banner sheet, i.e., the document pages which are to be printed immediately subsequent to that banner sheet (the print job identified by that banner sheet). This may provide a "real time" color correction for the color printer which is tailored to correct printing of the colors of the very next document to be printed.

Implementations of the various details and features disclosed herein may vary depending on the situation. Also, various of the disclosed features or components may be alternatively used for such functions as gray scale balancing, turning on more than one illumination source at once, such as oppositely positioned LEDs, etc.

It will be appreciated that these test patch images and colors may be automatically sent to the printer imager from a stored data file specifically designed for printing the dual mode banner sheet or other color test sheet page(s), and/or they may be embedded inside the customer job containing the banner page. That is, the latter may be directly electronically associated with the electronic document to be printed, and/or generated or transmitted by the document author or sender. Because the printed test sheet color patches and their printing sequence is known (and stored) information, the stand-alone spectrophotometer measurement data therefrom can be automatically coordinated and compared.

After the spectrophotometer or other color sensor reads the colors of the test patches, the measured color signals may be automatically processed inside the system controller or the printer controller to produce or modify the tone reproduction curve, for example, as explained in the cited references. The color test patches on the next test sheet may then be printed with that new tone reproduction curve. This process may be repeated so as to generate further corrected tone reproduction curves. If the printer's color image printing components and materials are relatively stable, with only relatively slow long term drift, and there is not a print media or other abrupt change, the tone reproduction curve produced using this closed loop control system will be the correct curve for achieving consistent colors for at least one or even a substantial number of customer print jobs printed thereafter, and only relatively infrequent and few color test sheets, such as the normal banner sheets, need be printed.

In addition to use in printers, it should be noted that color measurements, and/or the use of color measurements for various quality or consistency control functions, are also important for many other different technologies and applications, such as in the production of textiles, wallpaper, plastics, paint, inks, food products, etc. and in the measurement or detection of various properties of various materials, objects or substances. Thus, applications in various such other fields where these materials, objects or substances are to be color tested, including both (1) applications in which color measurements are taken and applied in a closed loop control system and (2) applications in which the measurement result is not fed back into a control loop, but is used to generate a one-time output, are contemplated.

FIG. 1 shows the reflectance spectra of twelve types of bond color reprographic papers measured with an Ocean Optics™ S2000 spectrophotometer equipped with a quartz halogen lamp at a light source at a color temperature of 3300° K. The twelve types of bond papers all have whitening additives added during their manufacture, and are specifically intended for color printing. All twelve types of bond papers exhibit very similar behavior in that incident flux between 350 and 410 mm is absorbed by the whiteners and subsequently reemitted as a fluorescent peak between 420 and 490 nm, with a pronounced peak located at approximately 435 nm. These regions are respectively labeled "UV Absorbtion Region" and "Fluorescence Emission Region" in FIG. 1. The fluorescent reemission in the blue region adds to the intrinsic, i.e. non-fluorescent, reflectivity, increasing the paper's radiance in this region and thereby making the paper appear whiter to an observer.

Figure 2:
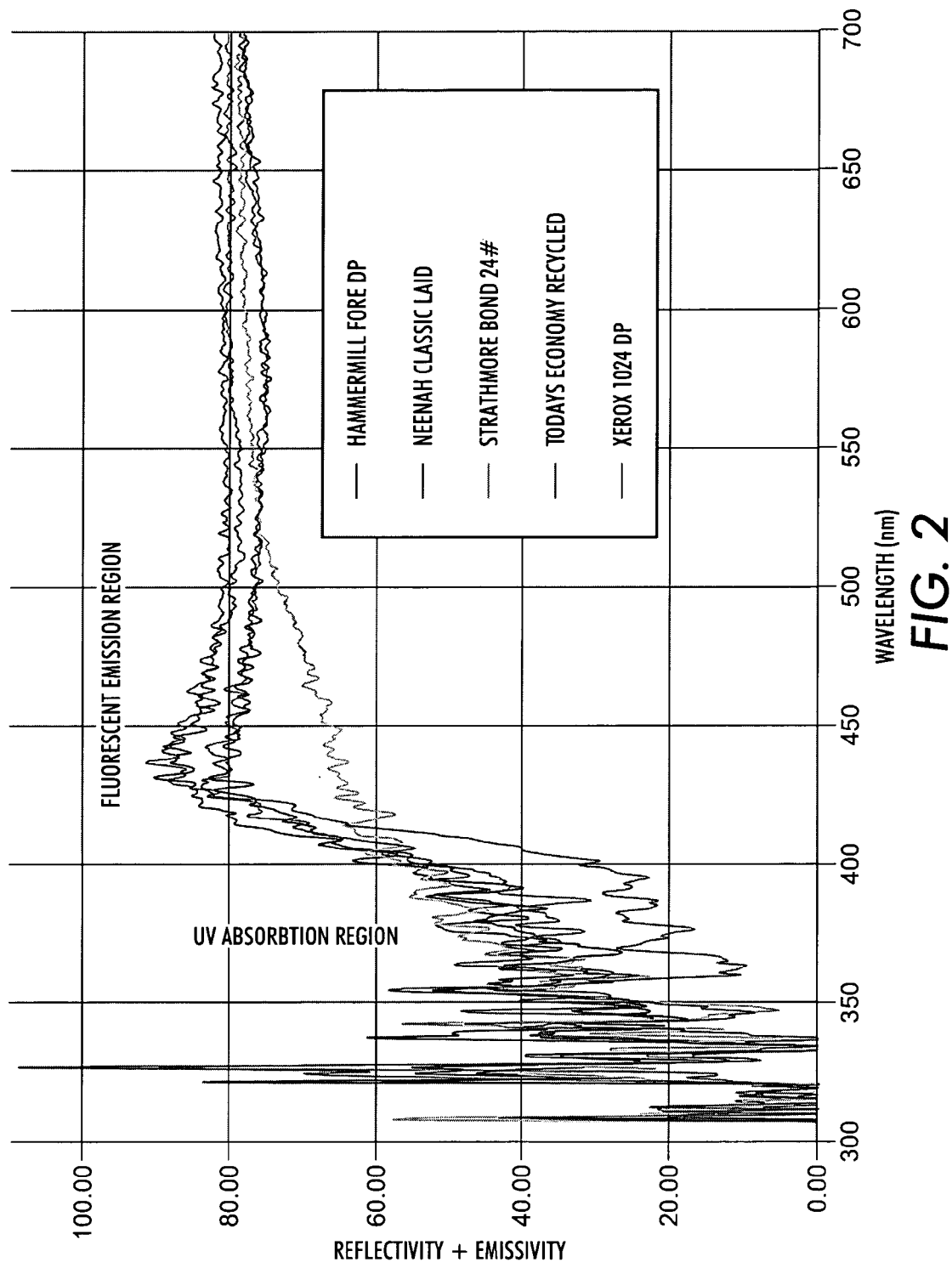
FIG. 2 shows the reflective spectra of five general purpose bond reprographic papers measured with an Ocean Optics™ S2000 spectrophotometer intended for monochrome or black on white imaging and printing.

FIG. 2 shows the reflective spectra of five general purpose bond reprographic papers measured with an Ocean Optics™ S2000 spectrophotometer. As a group, these five papers exhibit lower reflectivity than the 12 bond papers of FIG. 1, indicating lower levels of cleaning and bleaching during their manufacture. Additionally, they exhibit lower levels of fluorescence, and the Strathmore® Bond #24 paper exhibits neither fluorescent absorption nor emission, indicating the total absence of fluorescent whiteners. It may be inferred from the similarity of the reflectance of the Strathmore® Bond #24 paper to the other 4 types of papers above 550 nm, that if the whiteners were to be withheld from the other 4 types of papers, their reflectance spectra would be similar to Strathmore® Bond #24 paper.

Figure 3:
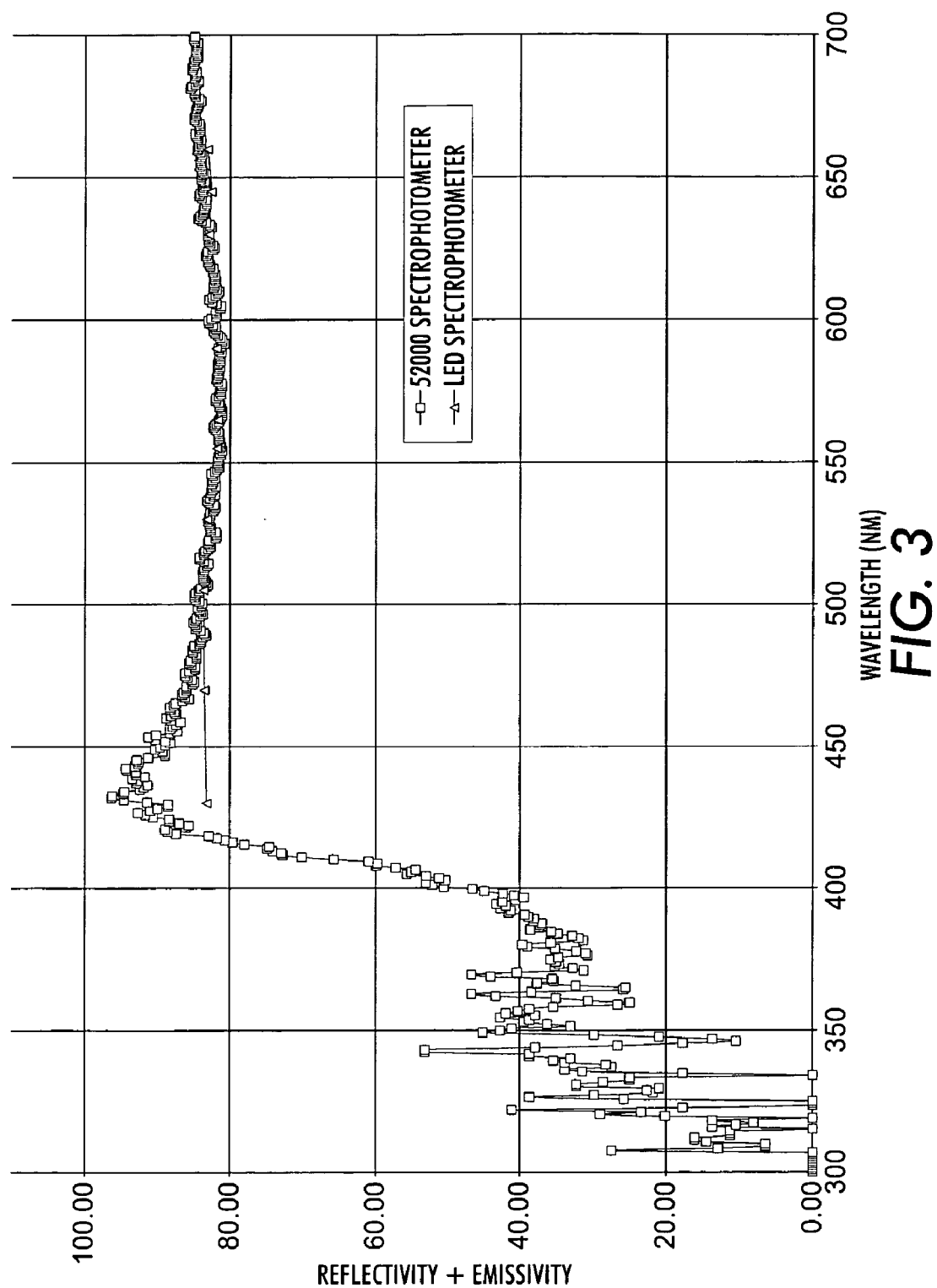
FIG. 3 shows the reflective spectra of particular fluorescent whiteness enhanced paper measured with a spectrophotometer having a UV light source and measured with an LED spectrophotometer not having a UV light source.

LED spectrophotometers generally use LEDs whose output spectra is visible and above 400 nm, and whose output spectra is therefore outside the range of wavelengths needed for fluorescent excitation. When spectrophotometers and colorimeters employing visible LEDs measure the color of fluorescent samples, the color coordinates are therefore lower in the blue region than when measured with devices using broadband sources. An example of this is shown in FIG. 3, which shows the reflective spectra of 24# Color Xpressions paper measured with an Ocean Optics™ S2000 Spectrophotometer and measured with the Xerox® spectrophotometer. The Ocean Optics™ S2000 spectrophotometer reports the pronounced peak at 435 nm and the trough at 370 nm characteristic of the presence of whiteners, whereas the Xerox® visible LED spectrophotometer does not.

Because an overwhelming majority of color images printed on paper are viewed under broadband illumination, the response of conventional LED based color measuring devices needs to be corrected in the blue region to account for their lower than viewed response in this region. If uncorrected, their reported color coordinates will be inconsistent with those observed and erroneous measurements will be reported.

As the amount of fluorescence differs among various classes of papers and also within classes of papers, a means of measuring the amount of fluorescence in paper being imaged is needed to enable accurate corrections to the measurements of conventional LED spectrophotometers.

A low cost means of measuring the fluorescence of paper in a reprographic engine may be provided, which may advantageously be able to perform the measurements in real time, even as the media in question travels through its sensing zone, for example, at speeds capable of exceeding 1000 mm/second.

Figure 4:
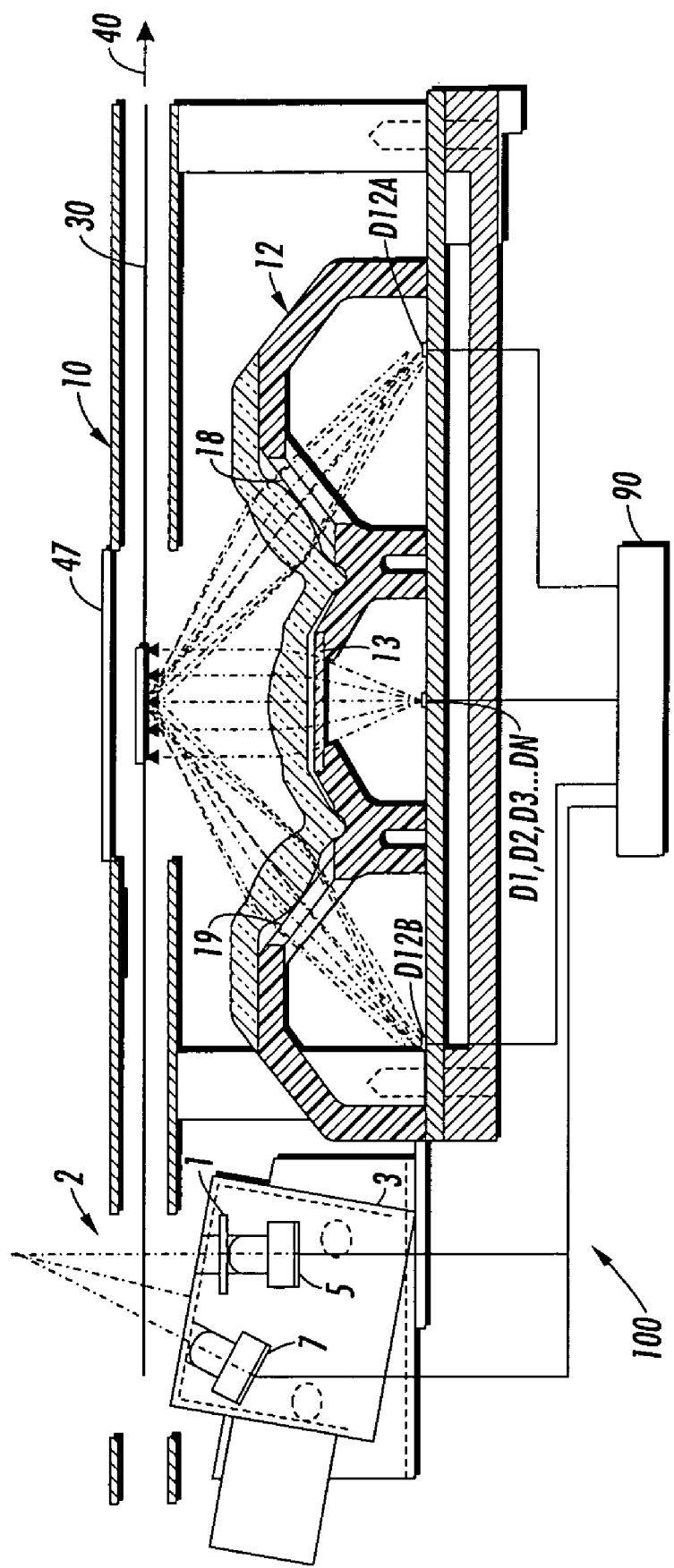
FIG. 4 is a cross-sectional view of an exemplary UV-enhanced LED spectrophotometer that includes a fluorescence sensor.

FIG. 4 is a cross-sectional view of an exemplary UV-enhanced LED spectrophotometer 100 measuring the color of a test patch of a test substrate 30 moving in an exemplary color printer output path with multiple photodetector chips, each with a perpendicular (in this view) orientation to put in the image plane of its optics, and thereby minimize image distortion. Reference is made in this regard to commonly assigned U.S. Pat. No. 6,621,576 and U.S. Patent Application Publication No. 2003/0142314, the subject matter of which is incorporated herein in its entirety, which disclose a visible band LED spectrophotometer similar to the visible portion of the disclosed UV-enhanced LED spectrophotometer shown in FIG. 4. In addition to a visible LED spectrophotometer portion 10, a UV LED spectrophotometer portion 2 may be provided which contains UV light emitting diode 7, with a peak emission wavelength of 370 nm and maximum emission wavelength of 410 nm, for example, which may be used to illuminate an untoned portion of a reprographic substrate 30, such as, for example, a sheet of paper. A portion of the diffuse reflection from the substrate 30 plus substrate fluorescent emission may be passed through a bandpass filter 1 and collected by linear integrated circuit (IC) 5. Bandpass filter 1 may have a 420 to 470 nm filtration, for example. The output of linear IC 5 may be linear with irradiance in the pass region of bandpass filter 1 and zero for radiation outside of this region. Thus, the signal provided by the linear IC may represent just the fluorescent light emitted by the substrate 30.

When substrate 30 is irradiated by the UV light emitting diode 7, some of the UV irradiance is absorbed by fluorescent whitener in the paper and reemitted in the blue region of the spectrum. The portion of reemitted emission that falls within the entrance aperture of the sensor housing 3 passes through bandpass filter 1 onto linear IC 5, where the portion of reemitted emission is converted to current and then amplified. UV light that is diffusely reflected by substrate 30 before being absorbed and reemitted may be blocked by bandpass filter 1 from reaching the detector because its wavelength is outside the passband of bandpass filter 1. UV light that is specularly reflected from substrate 30 is routed away from the entrance aperture of sensor housing 3 by the geometry of the optics, as the radiation is applied at an angle to the substrate 30, for example, at approximately 25 degrees, as shown in FIG. 4, and the detection may be performed normal to the surface of substrate 30. As noted above, the only light that is detected by detector 5 is the light from the substrate fluorescence excited by the UV LED.

Using databases constructed with and without UV LED illumination, linear IC 5 may advantageously be used to identify the existence and amount of fluorescence in color samples. The signal from linear IC 5 may therefore be used to ascertain the amount of fluorescence in reprographic papers, and readings from visible LED spectrophotometer 12 in the blue region can be adjusted to match that of industry standard devices using broadband illumination sources. Such databases may be constructed, for example, using an approach such as described in U.S. Pat. No. 6,721,629 or U.S. patent application Ser. No. 10/758,096, filed on Jan. 16, 2004, each of which is incorporated herein by reference in its entirety. The same approach may be used to construct databases for nine measurements.

The exemplary compact UV-enhanced spectrophotometer 100 shown in FIG. 4 has N different color sampling illumination sources, sequentially operated LEDs, D1 through DN, each with different color spectrum range outputs. For example, N may be 8. Each LED output may have the same simple condenser lens, such as lens 13, for directing the light from the respective LED onto the same test target area. Color filters for the LEDs may be provided in some cases if desired to further control the spectral range, but are not essential. The normal target area in the system may be, for example, an area of a printed color test patch or patches 31 on a sheet of paper 30 being otherwise normally printed and outputted. An alternate or calibration target area could be an unprinted area of the test paper sheet, or a white, gray, black or other color standardized test tile or surface such as 47 automatically (or manually) inserted into the effective field of view of the UV-enhanced spectrophotometer 100 when not blocked by a sheet 30.

The test target illumination by any one of the LEDs may provide a variable level of light reflected from that target depending on the colors of the test patch and the selected illumination source. A portion of that reflected light may be collected by a lens system such as 18 or 19 and focused by that lens system onto photosensor chips D12A and D12B to expose an array of multiple photo-sites having 3 or 4 different colors of filtering. FIG. 4 illustrates, with dashed line light rays, both the LED illumination and the focusing by the lens system (a simple two-element optic in this 18 or 19 example) onto the surface of photosensor chips D12A and D12B. Controller 90 is used to control illumination of LEDs D1, D2, . . . DN, and to control sensors 5, D12A and D12B.

When the patches are uniform, a ninth measurement from a UV LED may be used, eight measurements being provided from the other LEDs. The spectral reconstruction algorithm may use all nine measurements to accurately extract the reflectance spectra of the patches.

Figure 5:
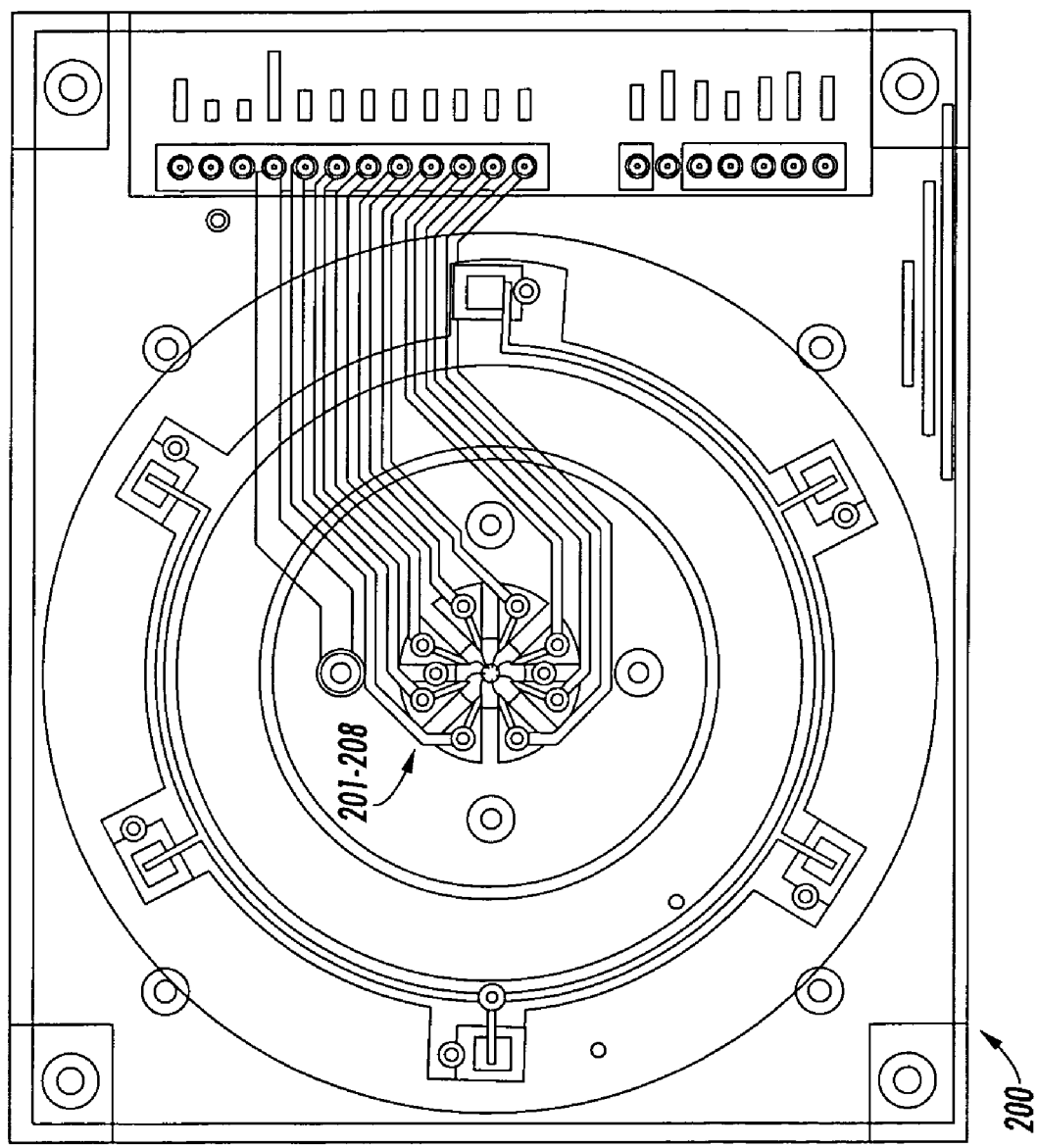
FIG. 5 is a plan schematic view of an exemplary LED spectrophotometer.

FIG. 5 is a plan schematic view of an exemplary visible LED spectrophotometer 200. As shown, the visible LED spectrophotometer 200 includes eight visible LEDs 201-208. The visible LED spectrophotometer 200 may be enhanced by including a UV LED along with corresponding circuitry and processing as needed.

Figure 6:
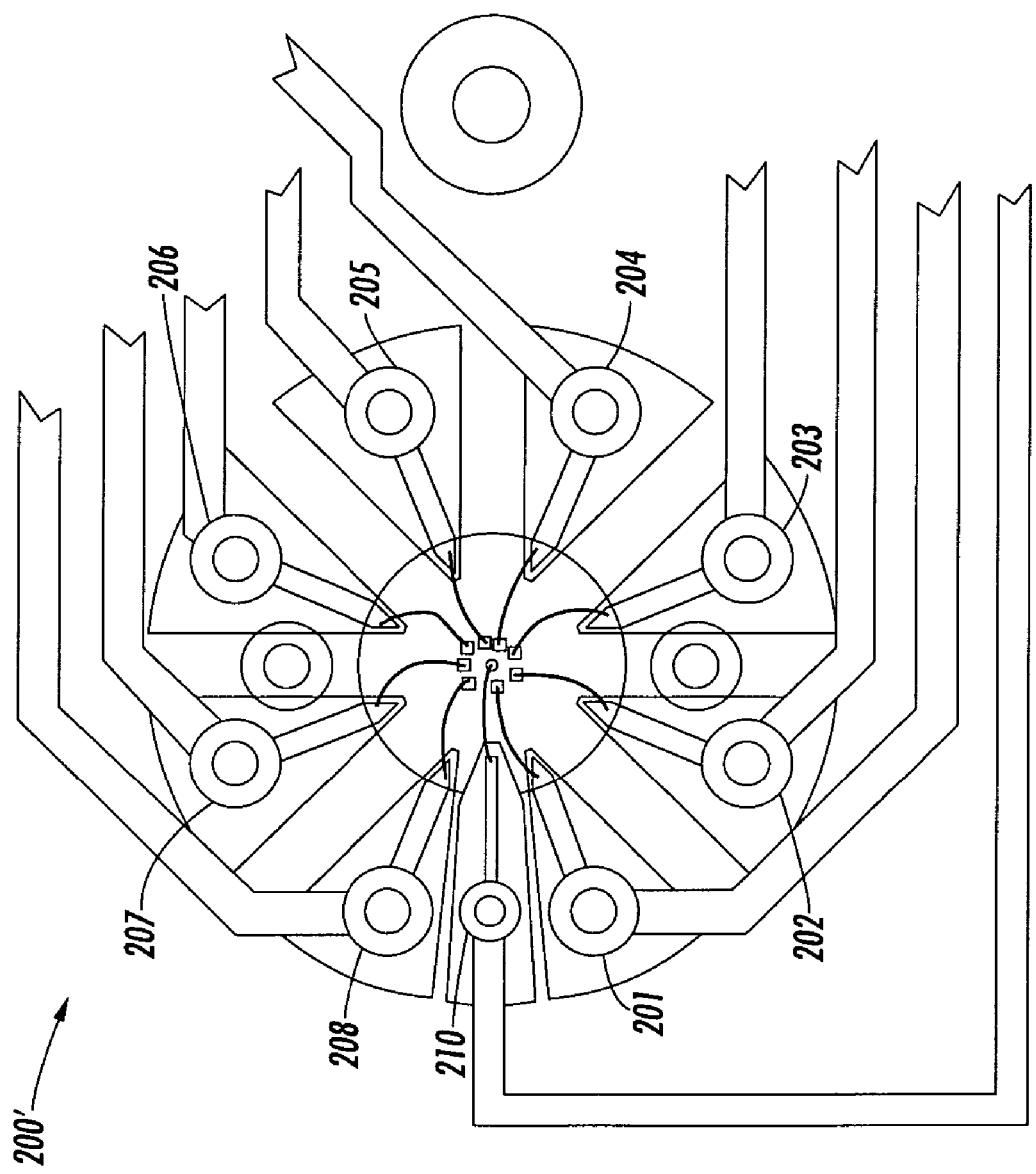
FIG. 6 is an enlarged partial schematic view of the spectrometer of FIG. 5, as modified to a UV-enhanced LED spectrophotometer that includes a fluorescence sensor.

For example, FIG. 6 shows an enlarged partial schematic view of the spectrometer of FIG. 5, as modified to a UV-enhanced LED spectrophotometer 200' that includes a UV LED 210 comprising a fluorescence sensor. In addition to the UV LED 210, the UV-enhanced LED spectrophotometer 200' includes a modified IR cutoff filter (not shown) to accommodate the expanded lower wavelengths provided by the UV LED 210. The modified IR cutoff filter may be in the form of a custom coating, for example, incorporated into a molded acrylic lens array by dip or evaporative methods. Similar methods may be used to add a coating to a glass substrate. Further, the standard grade of acrylic, such as Plexiglass® V825, suitable for the visible LED spectrophotometer 200 may be changed based on the particular UV LED 210 selected. For example, Plexiglass® V920 UVT or VS UVT may be appropriate. Glass substrates such as BK7 and Borofloat® may also exhibit sufficient UV transmittance for use in the UV-enhanced LED spectrophotometer 200'.

Although conventional glass or plastic lenses are illustrated in FIG. 4, it will be appreciated that fiber optics or selfoc lenses may be utilized instead in other applications. Fiber optics may be used to conduct the illumination from the LEDs. Also, a collecting fiber optic may be used if it is desired, for example, to space the detecting photosensor array remotely.

As utilized in the exemplary color sensing system 10, the low cost UV-enhanced spectrophotometer 100, as mounted in the printer 20 copy sheet output path 40, for example, may thus be part of a color correction system to automatically control and drive the printer 20 with respect to accurate CMYK color generation with a small number of printed test substrates, such as, for example, paper sheets 30. The color correction system can sequentially look at a relatively small series of color test patterns printed on copy sheets as they are output. One or more mathematical techniques for color error correction with multiple spectrophotometer-detected output color signals for each color patch as input signals can provide for a greatly reduced number of required printed test patches, for example, as shown in U.S. patent application Ser. No. 09/566,291, filed on May 5, 2000. That is, by recording the detector array multiple outputs when a test patch is successively illuminated by each individual LED, the reflectance of the test patch as a function of different wavelengths can be determined, and that reflectance of the test patch, as a function of different wavelengths, can be extrapolated or interpolated over the entire visible spectra. See, for example, in this regard, U.S. Pat. No. 6,449,045, which provides a low cost means of constructing full spectral curves using a LED spectrophotometer with a limited number of LEDs.

An accurate color control system, as disclosed herein, may thus regularly or almost constantly provide for testing and storing current machine color printing responses to color printing input signals (an up-to-date model) for remapping LAB (or XYZ) "device independent" color inputs (for later conversion to device dependent RGB or CMYK color space for printing). Such information may also be profiled into a system or network server for each different machine (and/or displayed on a CRT controller for color manipulation).

As further described in the above cross-referenced applications, the exemplary spectrophotometer 12 shown in FIG. 4 (or that shown in FIG. 5) may be desirably optically designed to be insensitive to the separation between the sensing head and the test patch target sheets, for example, by selecting the magnification of the target optic 18, 19, etc., to be approximately 1:1. (An exemplary focal length of those lens systems may be about 32 mm, for example, but is not so limited.) The degree of spatial insensitivity this provides allows non-contact measurements of moving printed sheets having variable distance spacings from the spectrophotometer 12, and thus allows for an unobstructed printer paper path. However, there may be some applications of this spectrophotometer in which displacement invariance is not important, in which case lenses may not be required.

As described in the above-cross-referenced applications, as a components-reversal alternative to the spectrophotometer shown in FIG. 4, the test patch 31 illuminations may be at 45 degrees to the surface of the media on which the color test patch is printed, and the sensing system may be detecting flux diffusely scattered from the (so-illuminated) test patch at 90 degrees (perpendicular to) that same color test patch surface. In such a configuration, central axis mounted photosensor chips D12A and D12B may be used.

Various technologies, architectures, and/or components may be used. For example, all of the LEDs D1, D2 . . . . DN may be provided by a single on-board chip or board. An appropriate selection of LED diodes with different wavelengths covering the visible spectrum may be formed, for example, in a circular pattern on a PWB.

As shown, the flux from each LED may be collimated and centrally directed to be applied to the same test patch area under the center of the spectrophotometer 12 by lens 13. That illumination position is also on the center axis of the lens 13. The lens 13 may be desirably located in the center of the ring or circle of photosensor chips D12A and D12B and their associated lens systems, as shown in FIG. 4.

Figure 7:
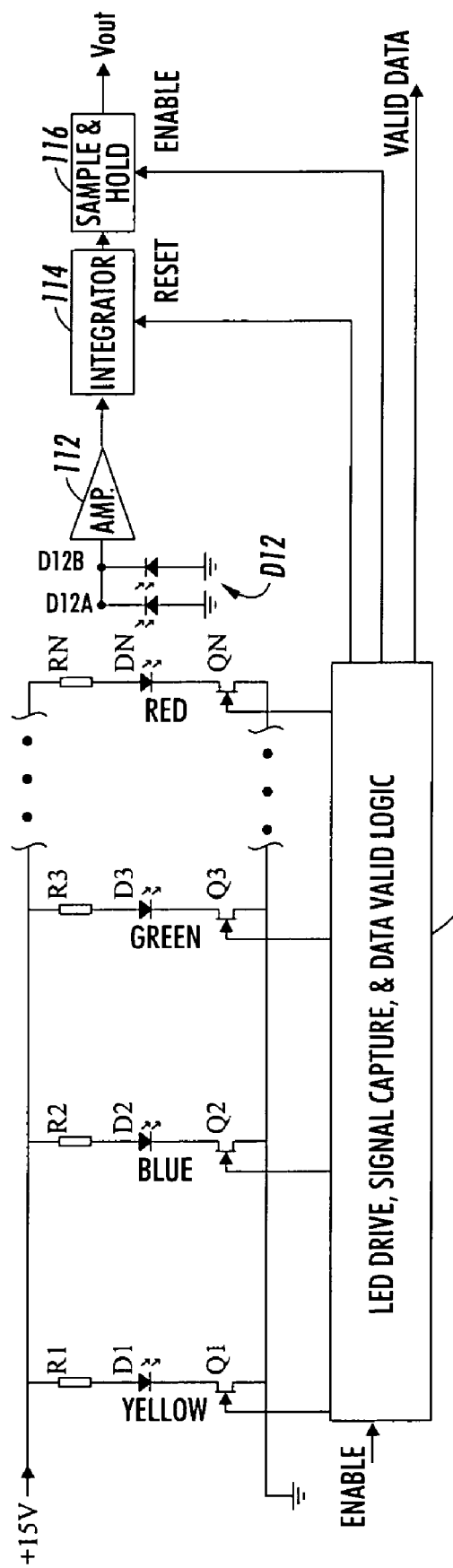
FIG. 7 schematically shows one example of circuitry for the exemplary UV-enhanced LED spectrophotometer of FIGS. 4 and 5.

FIG. 7 schematically shows one example of circuitry with which the exemplary UV-enhanced LED spectrophotometer of FIG. 4 (or that of FIG. 5) may be operated, portions of which are generally identified here for convenience as part of controller 90, even though the circuitry may be, in whole or in part, a separate circuit, desirably having a single driver chip for all of the LEDs in the spectrophotometer itself. In response to regular timing signals from a circuit 110 labeled "LED Drive, Signal Capture, & Data Valid Logic", each LED may be pulsed in turn by briefly turning on its respective transistor driver Q1 through Qn, by which the respective different spectra LEDs D1 through DN may be turned on by current from the indicated common voltage supply through respective resistors R1 through RN. N different exemplary light output colors of the N respective LEDs are indicated in FIG. 4 by the legends next to each of those LEDs. Thus, each LED may be sequenced one at a time to sequentially transmit light though the condenser lens 13 shown in FIG. 4.

While the LEDs in this example are turned on one at a time in sequence, it will be appreciated that the system is not limited to such an approach. There may be measurement modes in which it is desirable to turn on more than one LED or other illumination source at once on the same target area, for example.

As also illustrated in the exemplary circuit of FIG. 7, at the right hand side, the relative reflectance of each actuated LEDs color or wavelength may be measured by conventional circuitry or software for amplifying (112) and integrating (114) the respective signal outputs of the photodiode detector array of photosensor chips D12A and D12B, and directing this integrated signal information to a sample and hold stage 116. Stage 116 may provide an output signal Vout when released by an enabling signal input shown from circuit 110, which may also provide an accompanying "Data Valid" signal.

As discussed above, the corresponding LED pulsing and detector sampling rate is sufficiently non-critical and rapid for sampling each of multiple reasonable size color test patches moving by the spectrophotometer even for high speed media. However, by briefly pulsing the common LED driver voltage source to provide brief LED drive currents at a level above what is sustainable in a continuous current mode, higher flux detection signals may be obtained and the test patch may thus be interrogated in a shorter time period. In any case, by integrating the signal, such as with integrator 114, enhanced signal to noise ratios may be achieved. FIG. 7 shows merely one example of a relatively simple and straightforward circuit. Various alternatives or equivalent circuits may be readily implemented, for example, in an on-board hybrid chip or other architecture.

An additional conventional LED light emitter and detector may be integrated or separately mounted to detect black fiduciary or timing marks printed along one edge or margin of the substrate 30, if desired, thereby providing an enable signal for illumination and reading within the respective color test areas. Such fiduciary marks may be used to indicate the presence of an adjacent or parallel desired test area 31 then in the field of view of the UV-enhanced spectrophotometer 100. However, it will be appreciated that such fiduciary marks may not be needed and may not be desirable on certain media.

It is well known to use conventional optical filters of different colors for each of the respectively different color LED spectrophotometer target illumination sources. In particular, it is well known to use such color filters to exclude secondary emissions from LEDs, and/or to further narrow the output spectra of LED illumination sources. Such color filters are believed to be used for that purpose in some Accuracy Microsensors LED based commercial products, for example. However, it will be further appreciated that such color filters are not needed for those LEDs having sufficiently narrow bandwidths or for those LEDs which do not have secondary emissions that need to be suppressed. Therefore, filters may, but need not, be employed for the LEDs of the spectrophotometer.

Figure 8:
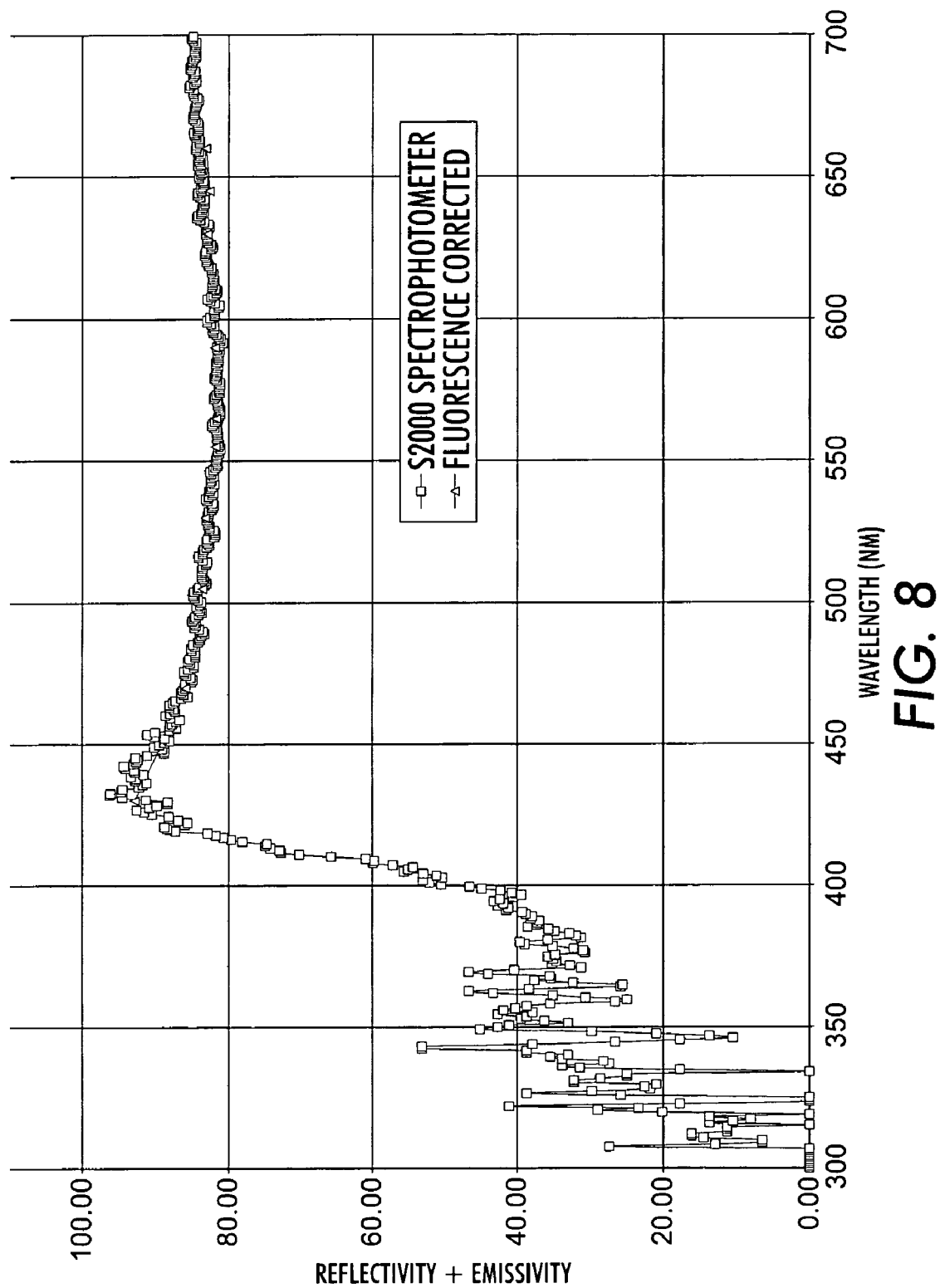
FIG. 8 shows the reflective spectra of a particular fluorescent whiteness enhanced paper measured with a UV spectrophotometer and measured with the exemplary UV-enhanced LED spectrophotometer of FIG. 4 with fluorescence correction.

FIG. 8 shows the reflective spectra of 24# Color Expressions paper measured with an Ocean Optics™ S2000 Spectrophotometer and measured with the exemplary UV-enhanced LED spectrophotometer of FIG. 4 with fluorescence correction. FIG. 6 thus shows the data of FIG. 8 with fluorescence correction applied by a UV-enhanced LED spectrophotometer. As shown in FIG. 8, the agreement between the readings of the UV-enhanced LED spectrophotometer and the Ocean Optics™ S2000 spectrophotometer are almost identical. Therefore, the exemplary UV-enhanced LED spectrophotometer of FIG. 4 advantageously increases the accuracy of conventional LED spectrophotometers by incorporating UV-LEDs, thereby matching the accuracy of conventional broadband-based instruments. The exact manner in which the fluorescence corrections are obtained may vary. For example, techniques such as disclosed in U.S. Pat. Nos. 6,449,045 and 6,584,435.

Various details have been described in conjunction with exemplary implementations outlined above. Various alternatives, modifications, variations, and/or improvements, whether known or presently unforeseen, are possible. For example, while the illustrative examples incorporate both visible and UV components, it is possible that a UV attachment for an existing visible spectrophotometer may be provided.

For example, an attachment for a visible spectrophotometer that determines the visible transmittance and/or reflectance spectrum of an object may comprise: a UV assembly having a UV LED light source, a UV filter, and a photodetector, the attachment adapted to be attached to the visible LED spectrophotometer and to measure fluorescence of the object in the visible spectrum; a mechanism to receive signals from the visible spectrophotometer and the UV assembly; and a mechanism to operate on the received signals to produce a full visible spectrum output that accounts for fluorescence of the object.

Accordingly, the exemplary implementations as set forth above are intended to be illustrative, not limiting.

What is claimed is:

1. An LED spectrophotometer device for determining an aspect of the color of an object, comprising:
a visible spectrophotometer comprising a plurality of light emitting diodes that emit light in the visible spectrum onto the object;
at least one detector for detecting said light after being directed onto the object and for generating an output;
a UV light emitting diode assembly that emits light in the near ultraviolet spectrum and communicates with at least one detector for generating an output; and
a mechanism that blocks light outside of a preselected visible blue spectral range from being detected by the detector of the UV light emitting diode assembly.

2. The device of claim 1, further comprising a processor that combines the outputs of the at least one detector of the visible spectrophotometer and the at least one detector in communication with the UV light emitting diode assembly.

3. The device of claim 2, wherein the processor is part of the UV light emitting diode assembly.

4. The device of claim 2, wherein the processor processes the outputs to generate an expanded reflectance spectrum.

5. The device of claim 1, wherein the UV light emitting diode assembly is separable from the visible spectrophotometer.

6. The device of claim 1, wherein the UV light emitting diode assembly is integrated with the visible spectrophotometer.

7. The device of claim 1, further comprising a triggering mechanism that utilizes output associated with the UV light emitting diode assembly.

8. A xerographic marking device incorporating the LED spectrophotometer device of claim 1.

9. An online color measuring system, comprising:
an online spectrophotometric measurement device that includes a plurality of visible light emitting diode light sources and provides output associated with the color of a moving object across the visible spectrum;
an ultraviolet light emitting diode assembly that illuminates the object and provides a fluorescence aspect of the color of the moving object in the visible spectrum; and
a mechanism that blocks light outside of a preselected visible blue spectral range from being detected by the detector of the UV light emitting diode assembly;
wherein the online color measuring system determines spectral reflectance of the moving object using the output of the online spectrophotometric measurement device and the fluorescence aspect from the ultraviolet light emitting diode assembly.

10. The system of claim 9, further comprising a processor that uses the output of the online spectrophotometric measurement device and the fluorescence aspect from the ultraviolet light emitting diode assembly to generate the spectral reflectance of the moving object across the visible spectrum.

11. The system of claim 10, wherein the processor uses the output of the online spectrophotometric measurement device and the fluorescence aspect from the ultraviolet light emitting diode assembly to determine a fluorescence adjusted reflectance in the visible spectrum of the moving object.

12. The system of claim 9, wherein the ultraviolet light emitting diode assembly is separable from the online spectrophotometric measurement device.

13. The system of claim 9, wherein the ultraviolet light emitting diode assembly is integrated with the online spectrophotometric measurement device.

14. The system of claim 13, further comprising a processor of the online spectrophotometric measurement device that determines a fluorescence adjusted reflectance spectrum.

15. The system of claim 9, further comprising a triggering mechanism that uses the output of the online spectrophotometric measurement device and the fluorescence aspect from the ultraviolet light emitting diode assembly.

16. A xerographic marking device incorporating the online color measuring system of claim 9.

17. A spectrophotometer for measuring a test substrate, comprising:
- a plurality of first light emitting diodes that emit light in the visible spectrum onto one or more color test portions of the test substrate,
- at least one first detector for detecting said light from one or more of the first diodes after being directed onto the test substrate and for generating an output;
- at least one second light emitting diode that emits light in the visible spectrum onto a timing mark portion of the test substrate;
- at least one second detector for detecting said light from the second diode after being directed onto the test substrate and for generating an output;
- at least one third light emitting diode that emits light in the near ultraviolet spectrum onto an untoned portion of the test substrate; and
- at least one third light detector for detecting said light from the third diode after being directed onto the test substrate and for generating an output.

18. A xerographic marking device incorporating the spectrophotometer of claim 17.

* * * * *